(12) United States Patent
Sherwin

(10) Patent No.: US 6,731,867 B1
(45) Date of Patent: May 4, 2004

(54) LENS PROTECTION MECHANISM

(75) Inventor: Daniel Sherwin, Jerusalem (IL)

(73) Assignee: Spintech Technologies, Ltd., Jerusalem (IL)

( * ) Notice: Subject to any disclaimer, the term of this patent is extended or adjusted under 35 U.S.C. 154(b) by 28 days.

(21) Appl. No.: 10/204,647

(22) PCT Filed: Nov. 15, 2000

(86) PCT No.: PCT/IL00/00750

§ 371 (c)(1),
(2), (4) Date: Dec. 4, 2002

(87) PCT Pub. No.: WO01/61406

PCT Pub. Date: Aug. 23, 2001

(30) Foreign Application Priority Data

Feb. 20, 2000 (IL) .................................................. 134630

(51) Int. Cl.⁷ .......................... G03B 11/00; G03B 17/00; G03B 17/08
(52) U.S. Cl. ......................... 396/25; 396/448; 396/544; 359/508
(58) Field of Search ................... 396/25, 448; 196/544; 359/508

(56) References Cited

U.S. PATENT DOCUMENTS

| | | | | |
|---|---|---|---|---|
| 2,298,063 A | * | 10/1942 | MacPherson | ............... 359/508 |
| 3,879,742 A | | 4/1975 | Smith | |
| 4,039,246 A | | 8/1977 | Voigt | |
| 4,148,551 A | | 4/1979 | MacAnally | |
| 4,497,550 A | | 2/1985 | Ouchi et al. | |
| 5,050,975 A | * | 9/1991 | Tsui | ............... 359/508 |
| 5,223,880 A | | 6/1993 | Rapp | |
| 5,315,333 A | * | 5/1994 | Nash | ............... 396/448 |
| 5,708,859 A | | 1/1998 | Tajima et al. | |
| 5,721,639 A | * | 2/1998 | Aoshima et al. | ............ 359/509 |
| 6,000,805 A | | 12/1999 | Inagaki | |
| 6,317,279 B1 | | 11/2001 | Chiang | |

FOREIGN PATENT DOCUMENTS

| | | |
|---|---|---|
| AU | 9515074 | 10/1996 |
| FR | 2 745 170 | 8/1997 |

* cited by examiner

Primary Examiner—Christopher Mahoney
(74) Attorney, Agent, or Firm—Feaster & Company

(57) ABSTRACT

A lens protecting mechanism (104), comprising: a transparent disc (122) having a rim (118); a plurality of wheels that engage and support the rim; and at least one motor, coupled to at least one of said wheels to apply rotational force to said disc (122).

16 Claims, 5 Drawing Sheets

LENS PROTECTION MECHANISM

RELATED APPLICATIONS

The present application is a U.S. national application of PCT/IL00/00750, filed Nov. 15, 2000.

FIELD OF THE INVENTION

The present invention is related to the field of lens protectors and especially centrifugal lens protectors.

BACKGROUND OF THE INVENTION

Cameras are required to operate under many adverse conditions, including flying particles, such as rain and snow. Rain and snow may adhere to the camera lens, reducing image quality.

One well known solution is to place a spinning glass disc before the lens, so that all the particles are captured by the disc. The centrifugal force generated by the disc as it rotates throws the particles towards the circumference of the disc, where they fall off and/or otherwise stop interfering with the image.

U.S. Pat. No. 3,879,742 to Smith, the disclosure of which is incorporated herein by reference, has the disc mounted on a central axis, with a surveillance camera at an off-axis location relative to the disc.

U.S. Pat. No. 5,223,880 to Rapp, the disclosure of which is incorporated herein by reference, integrates the disc with a rotor of a magnetic motor, with a casing surrounding the disc being the motor housing.

U.S. Pat. No. 5,315,333 to Nash, the disclosure of which is incorporated herein by reference, provides a single motor coupled to the disc using a band. The disc is mounted on two lines of bearings. The lens protection device is mounted on the camera, to isolate lens from gyroscopic and vibration forces.

Australian application 9515074, the disclosure of which is incorporated herein by reference, describes another band-based system, in which the disc is said to rotate at between 2600 and 3000 RPM. It is suggested to use a curved or hydrophobic surface to assist in water removal. The motor can be powered using the camera battery pack or using a separate battery.

SUMMARY OF THE INVENTION

An aspect of some embodiments of the invention relates to symmetric application of force to a rotating transparent disc. In some embodiments of the invention, this symmetry reduces vibration, thus possibly reducing wear, noise and/or image degradation. In other embodiments, asymmetric application of force and/or support is provided, possibly also achieving the desired results of reducing noise, wear and/or vibration.

In some embodiments of the invention, the rotational force is applied directly to the disc by one, two, three, four or more motors located at the circumference of the disc. In some embodiments of the invention, a plurality of wheels are distributed around the disc, engaging and/or supporting the disc. Each such wheel may be motor driven or free turning. Optionally, but not necessarily, the wheels are evenly distributed around the circumference of the disc.

An aspect of some embodiments of the invention relates to balancing angular moments in a centrifugal lens protection device. In some embodiments of the invention, by balancing angular moments, the magnitude of gyroscopic effects are reduced substantially. In some embodiments of the invention, the weight, radius and/or rotations speed of the disc and the motors and/or wheels used to rotate the disc are matched, such that a total angular moment is close to zero. Thus, for example, the total weight of a wheel may be twice the weight of the disc, to make up for a larger radius of the disc. In some embodiments of the invention, all the rotations are in a single plane. In some embodiments of the invention, the wheels are located at 45° to the horizontal and vertical axis, to better provide support for gyroscopic forces that are usually at about 45° to the axis of motion. In a camera, the axis of motion is expected to be parallel or perpendicular to the gravitational field. Optionally, the wheels locations may be flattened out to be more horizontal, thus providing a 4:3 ration as is common in TV cameras.

An aspect of some embodiments of the invention relates to electrical and mechanical coupling of motors for driving a rotating disc. In some embodiments of the invention, the motor windings of two or more DC motors are connected in series, such that mechanical mismatch of their speeds is compensated for by electrical voltage redistribution between the motors, without requiring any additional circuitry. Thus, both motors engage the disc equally, substantially without any slippage, even if there is some difference in radius between the wheels coupled to the motors and/or the disc is uneven. Another possible advantage is the ability to use lower quality motors whose design characteristics are not tightly controlled, without the adverse effect of added noise and/or vibration.

An aspect of some embodiments of the invention relates to a calibration step for a rotating disc lens protection device. In some embodiments of the invention, the disc is mounted on a small plurality of wheels. During a calibration step, the disc is rotated and the eccentricity of the wheels relative to their axes is corrected, thus reducing wear, vibration and/or noise.

An aspect of some embodiments of the invention relates to a transparent disc being easily removable for cleaning without taking apart the lens protector. In some embodiments of the invention, the transparent disc can be snapped off the engaging wheels, once a rim cover is removed.

An aspect of some embodiments of the invention relate to a method of connecting wheels for gripping a transparent disc, on a motor for rotating the wheels. In some embodiments of the invention, the wheels are supported by a case, which may also support the motor. The axis of the motor is coupled to one or more wheels, via a plurality of damping pins, such as rubber pins. In some embodiments of the invention, a plastic molding is provided on the axis and this plastic molding is pinned to the wheels. In some embodiments of the invention, by not supporting the disc on the motor, vibration coupling between the motor and the disc are reduced by the indirect connection between them.

There is thus provided in accordance with some some embodiments of the invention, a lens protecting mechanism, comprising:

a transparent disc having a rim;

a plurality of wheels that engage and support the rim; and at least one motor, coupled to at least one of said wheels to apply rotational force to said disc.

Optionally, said plurality of wheels comprises wheels having substantially identical mechanical properties. Alternatively or additionally, said plurality of wheels comprises four wheels. Alternatively or additionally, said al least one motor is coupled to said wheel using a rubber pin and wherein said motor does not substantially support said wheel against said disc. Alternatively or additionally, said wheels and said disc are constructed such that the angular inertia of the wheels substantially balances out the angular inertia of the disc. Alternatively or additionally, said wheels are arranged at substantially ±45° to expected movement axis of a lens for which lens protection mechanism is adapted.

There is also provided in accordance with some some embodiments of the invention, a lens protection mechanism, comprising:

a rotating transparent disc; and at least one counter-rotating object whose rotation substantially cancels out angular inertia caused by the rotation of the disc.

Optionally, said at least one counter-rotating object supports said disc. Alternatively or additionally, said at least one counter-rotating object applies rotational force to said disc.

There is also provided in accordance with some embodiments of the invention, apparatus for applying force to a rotating disc, comprising:

a first DC motor coupled to a first wheel for engaging said disc; and a second DC motor coupled to a second wheel for simultaneously engaging said disc; and wiring that connects said DC motors in series to a power source, such that the voltage distribution between the motors reflects the instantaneous rotational speed of each motor.

There is also provided in accordance with some embodiments of the invention, lens protection apparatus, comprising:

a rotating transparent disc;

at least one wheel, coupled to said disc and causing said disc to rotate; and a rim on said disc snap-connecting said disc to said apparatus, such that said disc can be snapped off said apparatus by applying pressure to the disc. Optionally, said rim is snap-connected onto said wheel. Alternatively or additionally, said rim is resilient.

BRIEF DESCRIPTION OF THE DRAWINGS

Non-limiting embodiments of the present invention are described below with reference to figures attached hereto. In the figures, identical structures, elements or parts that appear in more than one figure are generally labeled with the same or similar number in all the figures in which they appear. Dimensions of components and features shown in the figures are chosen for convenience and clarity of presentation and are not necessarily shown to scale. The figures are listed below.

DETAILED DESCRIPTION OF SOME EMBODIMENTS

Figure 1A:
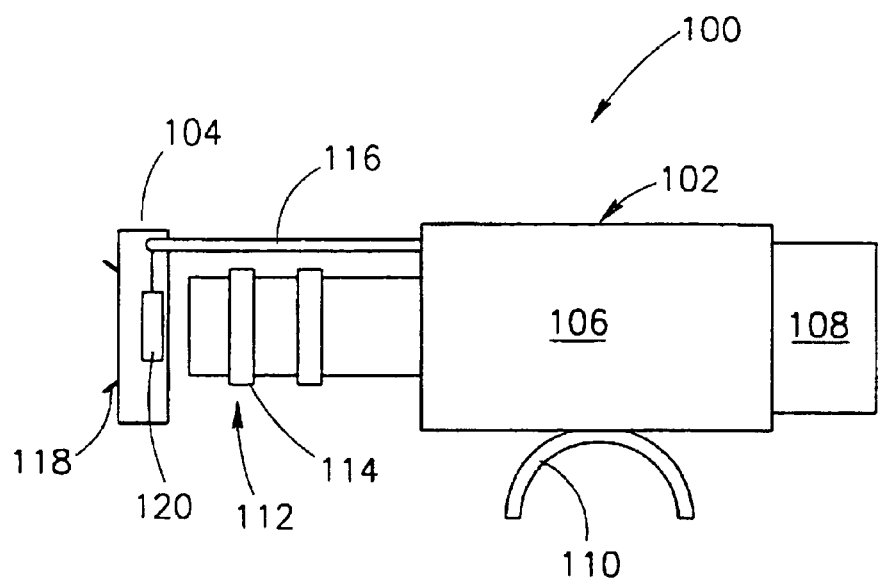
FIG. 1A is a side view of a lens protector mounted on a camera, in accordance with some embodiments of the invention.

FIG. 1A is a side view of a configuration 100 comprising a lens protector 104 mounted on a camera 102, in accordance with some embodiments of the invention. A typical, but not necessarily limiting application of a lens protector is for mounting on a camera. As shown in FIG. 1A, a typical camera 102 comprises a body 106, a battery 108, a shoulder grip (or hand grip) 110 and a lens 112. In a manual or automatic focus camera, a focus (and/or zoom) ring control 114 is optionally provided.

As shown, lens protector 104 is placed in front of lens section 112, and is optionally coupled by a coupler 116 directly to body 106 of the camera. An optional control box 120, which can include a power source, electronic and/or manual controls, which may be mounted on protector 104, is shown as well. Optionally, a flared rim 118 is provided to guide removed water and debris away from the camera. Not shown are a plurality of optional openings in the bottom of protector 104, for draining of water that may enter the protector.

Figure 1B:
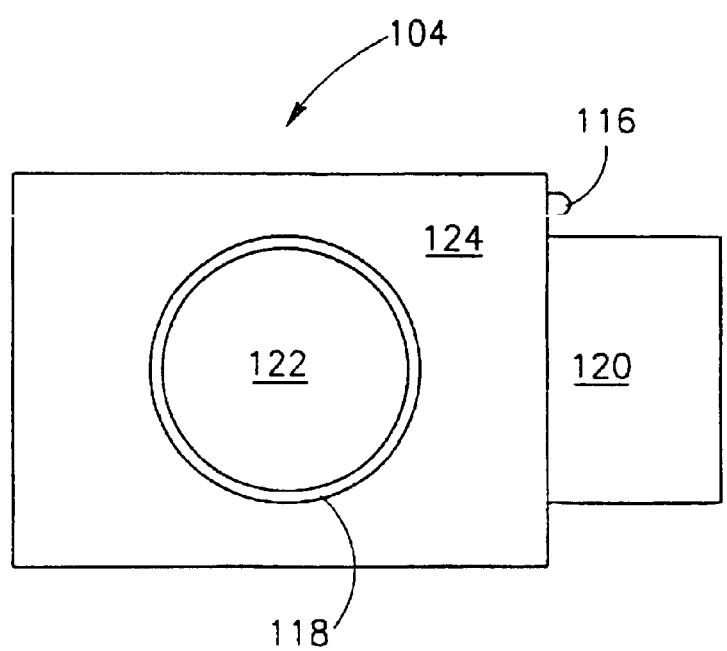
FIG. 1B is a front view of a lens protector, in accordance with some embodiments of the invention.

FIG. 1B is a front view of lens protector 104, in accordance with some embodiments of the invention. A disc 122 is centrally located inside flared rim 118. A housing 124 is shown enclosing the mechanism of protector 104 (described below). Disc 122 is optionally made of optically transparent glass. As used herein, "transparent" means: allowing the passing through of sufficient energy of the relevant wavelengths of electromagnetic radiation for forming an image by the camera. In some embodiments transparent disc 122 may be coated, for example to reduce reflection. Disc 122 may have filtering functionality, for example a "grey", a UV, a polarizing, or a "neutral density" filter. In some embodiments disc 122 may be a lens.

Alternatively or additionally, in some embodiments, protector 104 is integrated with lens section 112 or camera 102, rather than being a separate device.

Figure 2:
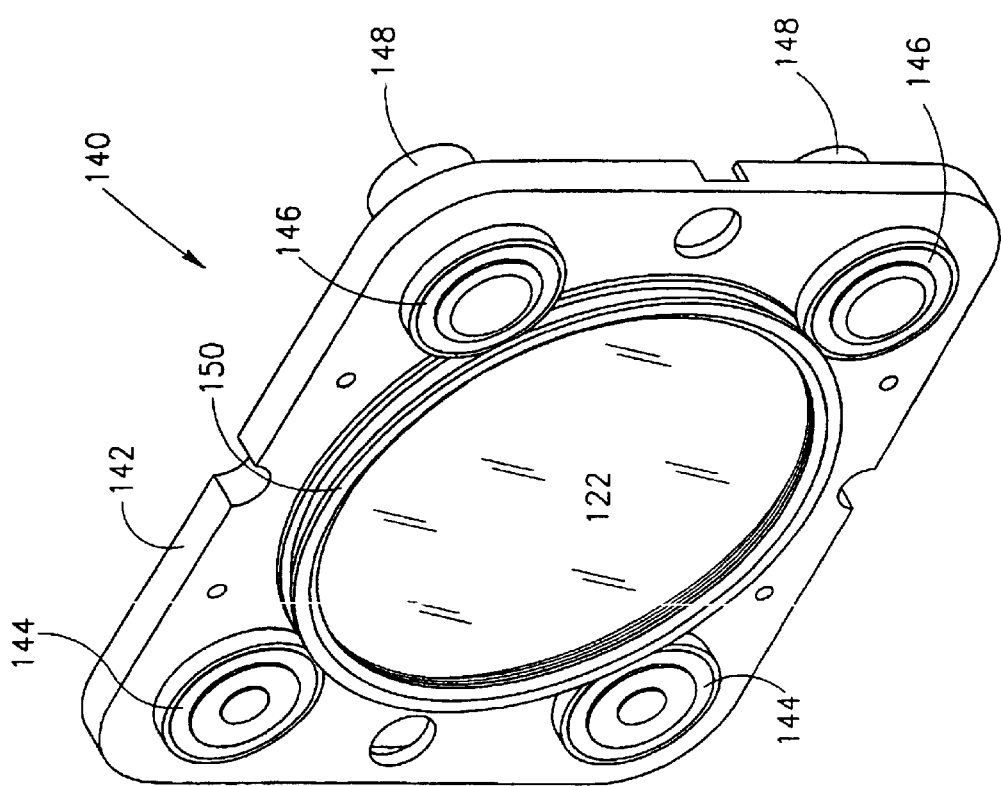
FIG. 2 is a perspective view of a main subassembly of the lens protector of FIG. 1, showing the moving parts of the protector, in accordance with some embodiments of the invention.

FIG. 2 is a perspective view of a main subassembly 140 of lens protector 104, showing the moving parts of protector 104, in accordance with some embodiments of the invention. A rigid body element 142, which is coupled to housing 124, optionally has mounted thereon a plurality of free turning wheels 144 and a plurality of motorized wheels 146, powered by a plurality of motors 148. In some embodiments of the invention, body element 142 is attached to housing 124 via a plurality, such as four, of rubber pins, for example pins having a shear strength of 55 and a diameter of 6 mm. Body element 142 is optionally made of metal, however other materials, such as plastic and hard rubber may also be used.

A ring 150, is engaged by wheels 144 and 146 and couples between the wheels and transparent disc 122. Optionally, transparent disc 122 is mounted on ring 150. Alternatively, ring 150 may be an outer edge of disc 122.

In some embodiments of the invention, wheels 146 supply power to rotate ring 150 and disc 122, while wheels 144 act as bearings for the rotational motion.

Several problems, including noise and reduced image quality can be caused by the vibration of protector 104 and/or the coupling of such vibration to camera 102.

In some embodiments of the invention, the arrangement of wheels, the design of the wheels and/or the mechanics of the wheel coupling to body 142 is symmetrical or asymmetric around ring 150. This, and/or other features described below are optionally provided for reducing the vibration of protector 104. It is noted that by using same elements (the wheels) to hold, balance and rotate disc 122, proper design of the wheels and their balancing can be more easily achieved than if separate elements are used for each function. However, this is not an essential feature of the invention, albeit a desirable one. It is noted that in the design shown in FIG. 3 and FIG. 4, both motorized and free-tuning wheels provided exactly the same support to disc 122 and differ only in that the motorized wheels also provide power.

What is shown in FIG. 2 is a two way symmetry (around vertical and horizontal axes), however complete symmetry (also rotational) may also be provided. Alternatively or additionally to providing four wheels, a different number of wheels, for example three may be provided. The design shown is optionally used so that the wheels are located at expected directions of application of gyroscopic force. This force is expected to act at about 45° to the main movement axes, which in cameras, are usually parallel and perpendicular to the gravitational field and disc 122.

Alternatively or additionally to vibration coupling problems, gyroscopic inertia of the protector may also be a problem, especially if a rotational speed of 2000–3000 RPM, or higher, such as 3000–4000 RPM is provided. It is expected that various features described herein may be used in the design of lens protectors with higher rotational speeds and/or larger sizes, utilizing the advantages that may be achieved, for example as described herein.

In some embodiments of the invention, the protector is designed so that the angular moment of the moving parts substantially cancels itself out. To that effect, the weight (and radial distribution of the weight) of the wheels is matched to the weight of the disc, taking into account the relative radii of the wheels and disc. Thus, as the wheels turn in opposite direction to the disc, the angular moments of the wheel scan cancel out those of the disc, even when the rotation is started. In an exemplary embodiment, the disc weighs 17 grams and the wheels, each, weigh 28 grams. Alternatively, the disc angular moment is canceled out by a second disc having a similar radius and rotating in an opposite direction.

Figure 3:
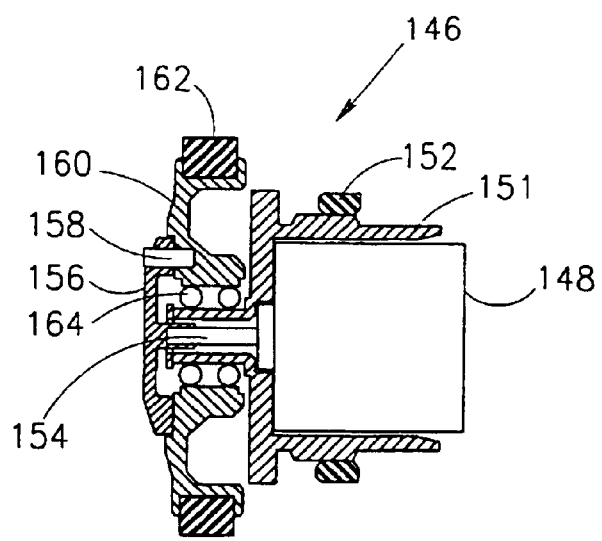
FIG. 3 is a cross-sectional view of a motorized wheel, in accordance with some some embodiments of the invention.

FIG. 3 is a cross-sectional view of an exemplary motorized wheel 146, in accordance with some embodiments of the invention.

Figure 4:
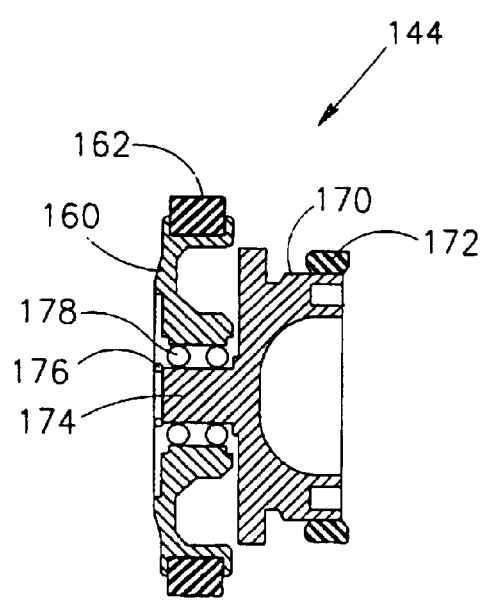
FIG. 4 is a cross-sectional view of a free-turning wheel, in accordance with some some embodiments of the invention.

FIG. 4 is a cross-sectional view of an exemplary free-turning wheel 144, in accordance with some embodiments of the invention.

Although the motorized wheels 146 and the free-turning wheels 144 can differ in several respects, as described below, in some embodiments of the invention, a substantially same wheel rim 162 is provided in both wheel types for engaging ring 150. Alternatively or additionally, a substantially same wheel body 160 optionally is provided in both wheel types. In some embodiments of the invention, the wheels are coupled to body plate 142 in a same manner, by a casing, on which the wheels are axially mounted. The casing optionally includes a flange so that the casing can be coupled to body plate 142 by a nut the engages the body plate between the nut and the flange. The casing may be eccentric, for example for the free-turning wheels, allowing correction of the distance between the wheel centers.

In some embodiments of the invention, wheel rim 162 is formed of a low distortion and compression material, which also optionally has suitable friction characteristics for engaging ring 150, for example thermo-rubber. In some embodiments of the invention, wheel rim 162 is required to be precision made, and to maintain its dimensions over a normally encountered range of humidity and temperature, for example between −40° C. and +50° C. and between 1% and 100% relative humidity. In some embodiments of the invention, wheel rim 162 is formed of a cast thermo-rubber that is also selected to have a high damping factor, so as to reduce resonance effects.

In an exemplary embodiment, the above rubber is first molded (with vulcanizing) on the wheels, then machined and then ground to the exact desired shape. These processes are typically required due to the relatively low tolerances achieved with standard rubber manufacturing techniques, while it is desirable to have very precise machining, for example no more than 4 micron run off, although 10 microns run-off may also be acceptable.

Various considerations may be taken into account during manufacturing, to reduce distortion caused by the manufacturing processes. In one example distortions of the wheels caused by molding the rubber may be prevented by molding the wheel rims while the wheel is not completely machined (using CNC) and then completing the machining after the molding, and optionally, before the grinding of the wheel rim.

As illustrated in FIG. 3 a plastic molding 156 is optionally attached to an axis 154 of the motor. Optionally, molding 156 is coupled to wheel 160 using rubber pins, one pin 158 being shown. Optionally, three pins are used. A casing 151 is optionally provided, which grasps motor 148 and optionally surrounds axis 154. In a space 164 formed between casing 151 and wheel 160, a plurality of ball bearings are optionally provided. Wheel 160 is optionally locked onto (and supported by) casing 151 (and optionally not axis 154) by a locking ring. Casing 151 is optionally coupled to body 142 by compression, between a flange of casing 151 and a locking nut 152. In some embodiments of the invention, casing 151 is movable in the plane of body 142, for example casing 151 being eccentric, so that axis 154 can be moved relative to disc 122. Alternatively to rubber pins 158, a slip-contact may be provided between wheel 160 and plastic molding 156.

FIG. 4 illustrates a free turning wheel 144, in which a wheel 160 is mounted on a hinge 174, formed of a casing 170. A locking ring 176 is optionally provided to lock the wheel on the axis. A spacing 178 formed between wheel 160 and hinge 174 optionally contains ball bearings. Casing 170 is optionally locked to body 142 in a same manner as is casing 151 (FIG. 3), using compression between a flange and a locking nut 172. Alternatively or additionally to motorized wheels, some of the free-turning wheels may include means for moving casing 170 relative to body 142.

Figure 5:
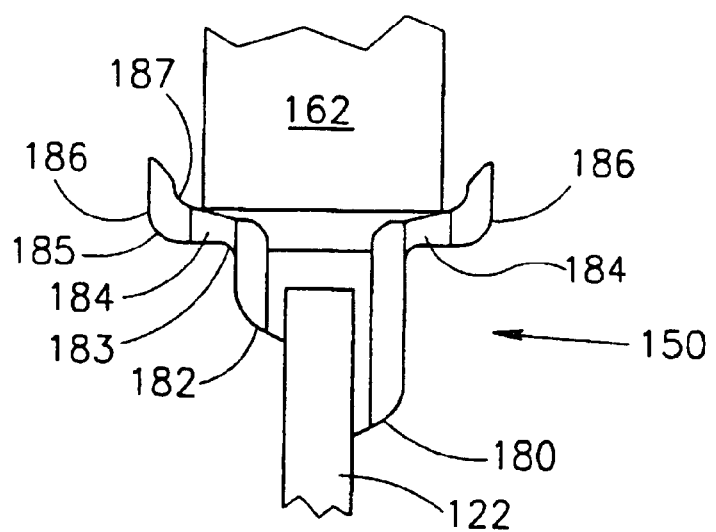
FIG. 5 is a cross-sectional view of a ring for coupling a disc to the wheels of FIGS. 3 and 4, in accordance with some embodiments of the invention.

FIG. 5 is a cross-sectional view of ring 150, used for coupling disc 122 to wheels 144 and 146, in accordance with some embodiments of the invention. As shown, disc 122 is held between a back lip 182 and a front lip 180. Wheel rim 162 is held between two side rims 186. In some embodiments of the invention, an inclined portion 184, is provided, to be in contact with the edge of wheel rim 162, to stabilize disc 122 relative to wheel rim 162. In an exemplary embodiment of the invention, the lips 180 and 182 of disc-holder 150 are at an oblique angle to the surface of disc 122. Alternatively or additionally, the angles 183 between portions 184 and portions 180 and 182 are rounded. Alternatively or additionally, the edge 185 of portion 186 is rounded. Alternatively or additionally, edge 187 of portion 186 is rounded, or alternatively has an straight section starting at the edge and terminating curve which blends into the inclined surface of portion 184.

In some embodiments of the invention, ring 150 is made of Delarin and has a run out tolerance of 20 micron. In some embodiments of the invention, ring 150 is heated, for example to 50° C. or 70° C. before being pushed into the space between lips 182 and 180, thus expanding ring 150 and allowing easier insertion of disc 122. Once disc 122 is inserted, it optionally straightens out the ring. In some embodiments of the invention, the use of a resilient plastic, and especially of the resilience of rims 186, allows the disc to be snapped off of the wheels, without taking the entire lens protector apart. Alternatively or additionally, ring 150 absorbs vibration.

Disc 122 is optionally formed of plate glass and ground to have a radial accuracy of 20 microns and a thickness variation of less than 1%. However, these numbers may vary depending on the application.

Figure 6:
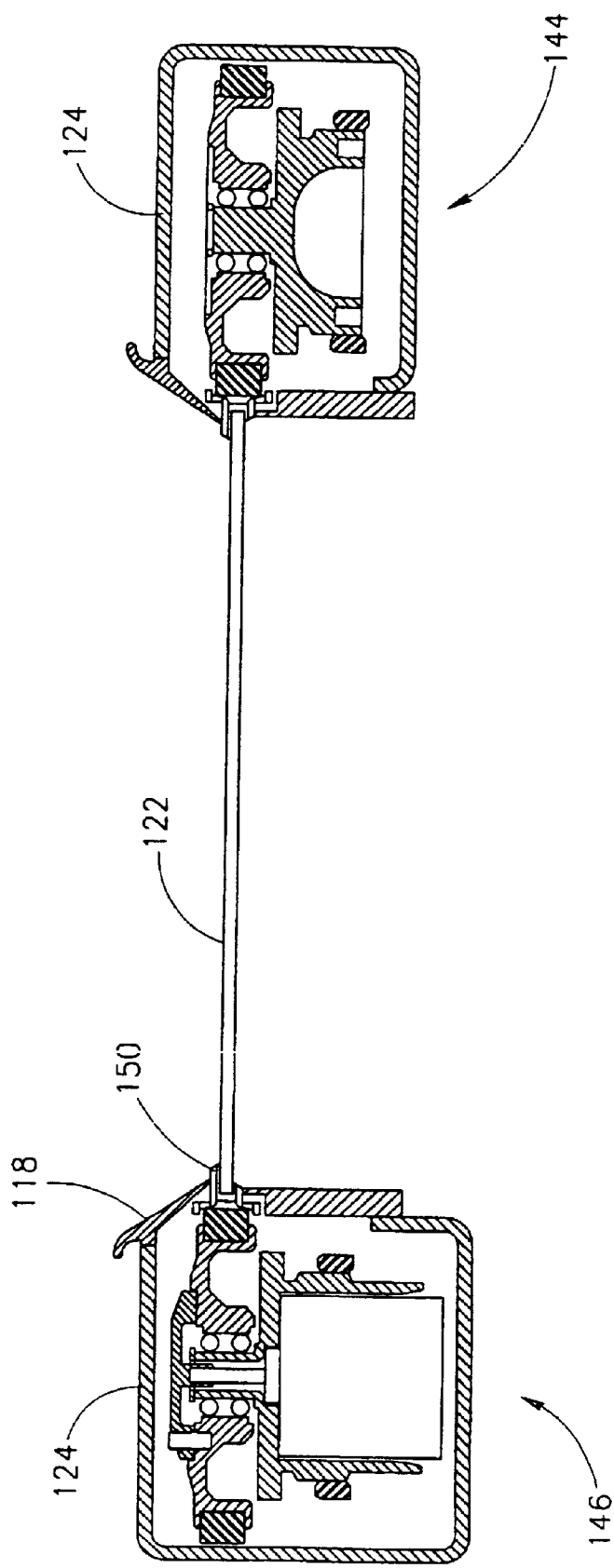
FIG. 6 is a cross-sectional view through the lens protector of FIG. 1B, cutting across one motorized wheel, through a transparent disc and a free-turning wheel in accordance with some embodiments of the invention.

FIG. 6 is a cross-sectional view through lens protector 104, cutting across one motorized wheel 146, through the center of disc 122 and a free-turning wheel 144. As can be seen the casing surrounding the motorized wheel is generally larger than the casing surrounding the free-turning wheel. Optionally, the attachment to camera 102 is at the side of the motorized wheels. Alternatively, the attachment is between the bottom of the lens protector and camera body 106. In some embodiments of the invention, the coupling is directly to camera body 106, to reduce the transmission of vibrations to the lens of camera 102.

In some embodiments of the invention, the motors are powered by the battery of the camera, for example being fed off of an existing power socket in the camera (e.g, a projector lamp socket). Alternatively, the motors are connected directly to the camera power supply. Alternatively, a battery, in some embodiments rechargeable, is provided integral with lens protector 104, optionally inside of housing 124, for example in box 120 (FIG. 1).

In some embodiments of the invention, the two or more DC motors are electrically connected in series, in addition to them being mechanically coupled via ring 150. This interconnection allows the motors to distribute the available voltage between themselves, without requiring an external control circuit. For example, if one wheel has a smaller radius than the other wheel the motor coupled to the larger wheel needs (and will receive) a lower voltage than the smaller wheel and slippage will be prevented. This distribution of voltage to prevent slippage (and associated wear, noise and vibration) optimally compensates for differences in the wheel radius without requiring exact calibration of motor rotation speeds. Additionally, this redistribution may also compensate for variations in wheel and disc diameters.

As noted above, an on/off switch may be provided on control box 120. Protector 104 may be configured in several ways. It may be an automatic device that is on at all times. Alternatively, it may be manually switched on and off, using said switch. Alternatively, protector 104 may be automatic, for example switching on when any debris or water is detected on disc 122. In some embodiments of the invention, the humidity inside or outside protector 104 is monitored. If the humidity approaches 100%, it is assumed that wet conditions apply and lens protector 104 is activated.

In some embodiments of the invention, the switch is located on lens protector 104, adjacent where the camera operator's fingers are located during operation of the camera. Alternatively, the switch is connected to lens protector 104 by a wire and is located on camera body 106 or even on lens section 112. Optionally, the switch is adhesive and can be attached to any desired location on the camera. Possibly, a wireless switch is provided, alleviating the need to keep the wire out of the way.

The above lens protector has been described mainly for hand-held cameras. However, such protection may also be provided for other types of cameras, for example industrial cameras and surveillance cameras. Optionally, detection of debris or water on disc 122 is by image processing the image acquired by the camera, for example by detecting reduction in focus quality. Alternatively or additionally, the disc may be slowly rotated and changes in the image correlated with the disc rotation can be used to determine the presence of debris or water. The use of image processing is especially indicated in setting where the image is automatically processed for other reasons, such as surveillance.

It should be appreciated that in some application, for example industrial imaging, noise is less of a problems, so tolerances, especially of run-outs may be poorer. Also, there may be fewer restrictions of the weight of protector 104. For example, noise can be reduced by making disc 122 thicker, since a thin disc acts as a membrane for the acoustic vibrations in protector 104. However, such a thickening will increase the weight of protector 104, as also the wheel will need to be increased substantially in weight.

It is generally expected that the run-out tolerances affect the noise, but do not substantially affect the gyroscopic properties of the lens protector. In an exemplary reduced quality application, a wheel run-out of 30 microns and a disc/ring run-out of 100 micron, will still operate, albeit with increased noise and possibly wear and vibration.

In one manufacturing method, the parts are first cast or injected and then machined using CNC and then a quality check is made to reject parts that are out of tolerance. Depending on the desired quality, one or more of the quality enhancing steps may be omitted or reduced in strictness. It is however noted that by using poorer tolerances, a reduction in life time of the lens protector may also result.

Optionally, a thermostat may be provided, for heating disc 122, for removing condensation on disc 122 and on lens 112. Disc 122 may be heated, for example, using radiation heaters, inside of housing 124. Alternatively, spinning disc 122 will remove such condensation.

In a medical application, a lens protector is provided for protecting endoscope lens inside the body. In an exemplary application, the outer diameter is between 10 and 20 mm, however, smaller devices, such as 5 mm or smaller may also be provided. Generally, the manufacturing will be simpler, as noise and/or longevity may not be important consideration and tolerances may be easier to achieve as the parts have a smaller self weight.

It will be appreciated that the above described methods of protecting lens and the various apparatus described may be varied in many ways. In addition, a multiplicity of various features, both of methods and of devices have been described. It should be appreciated that different features may be combined in different ways. In particular, not all the features shown above in a particular embodiment are necessary in every similar embodiment of the invention. Further, combinations of the above features are also considered to be within the scope of some embodiments of the invention. When used in the following claims, the terms "comprises", "includes", "have" and their conjugates mean "including but not limited to".

What is claimed is:

1. A lens protecting mechanism, comprising:
    a transparent disc having a rim;
    a plurality of wheels that engage and support the rim; and
    at least one motor, coupled to at least one of said wheels to apply rotational force to said disc.

2. A mechanism according to claim 1, wherein said plurality of wheels comprises wheels having substantially identical mechanical properties.

3. A mechanism according to claim 2, wherein said wheels and said disc are constructed such that the angular inertia of the wheels substantially balances out the angular inertia of the disc.

4. A mechanism according to claim 1, wherein said plurality of wheels comprises four wheels.

5. A mechanism according to claim 4, wherein said wheels and said disc are constructed such that the angular inertia of the wheels substantially balances out the angular inertia of the disc.

6. A mechanism according to claim 1, wherein said at least one motor is coupled to said wheel using a rubber pin and wherein said at least one motor does not substantially support said wheel against said disc.

7. A mechanism according to claim 6, wherein said wheels and said disc are constructed such that the angular inertia of the wheels substantially balances out the angular inertia of the disc.

8. A mechanism according to claim 1, wherein said wheels and said disc are constructed such that the angular inertia of the wheels substantially balances out the angular inertia of the disc.

9. A mechanism according to claim 1, wherein said wheels are arranged at substantially ±45° to expected movement axes of a lens for which the lens protection mechanism is adapted.

10. A mechanism according to claim 1, further comprising:
    at least one counter rotating wheel whose rotation substantially cancels out angular momentum caused by the rotation of the disc.

11. A mechanism according to claim 10, wherein said at least one counter rotating wheel is connected to said motor.

12. A mechanism according to claim 1, wherein said at least one motor is a DC motor;
    and further comprising:
    a second DC motor coupled to a second wheel for simultaneously engaging said disc; and
    wiring that connects said DC motors in series to a power source, such that the voltage distribution between the motors reflects the instantaneous rotational speed of each motor.

13. A mechanism according to claim 1, wherein said rim is removably snap-connecting said disc to said engaging wheel, such that said disc can be snapped off said engaging wheel by applying force to the disc.

14. Apparatus according to claim 13, wherein said rim is snap-connected onto said wheel.

15. Apparatus according to claim 13, wherein said rim is resilient.

16. Apparatus according to claim 1, in which the some or all of the angles and edges of said rim coupling of the motor to said rotating transparent disc are rounded.

* * * * *

UNITED STATES PATENT AND TRADEMARK OFFICE
CERTIFICATE OF CORRECTION

PATENT NO. : 6,731,867 B1 Page 1 of 1
DATED : May 4, 2004
INVENTOR(S) : Daniel Sherwin It is certified that error appears in the above-identified patent and that said Letters Patent is hereby corrected as shown below:

Column 10,
Line 29, after "which" remove "the"

Signed and Sealed this

Twenty-third Day of November, 2004

JON W. DUDAS
*Director of the United States Patent and Trademark Office*